US 10,117,767 B2

(12) United States Patent
Krahenbuhl

(10) Patent No.: US 10,117,767 B2
(45) Date of Patent: Nov. 6, 2018

(54) ANKLE SUPPORT

(71) Applicant: Doug Krahenbuhl, Alpine, UT (US)

(72) Inventor: Doug Krahenbuhl, Alpine, UT (US)

(*) Notice: Subject to any disclaimer, the term of this patent is extended or adjusted under 35 U.S.C. 154(b) by 436 days.

(21) Appl. No.: 14/866,296

(22) Filed: Sep. 25, 2015

(65) Prior Publication Data

US 2016/0089259 A1 Mar. 31, 2016

Related U.S. Application Data

(60) Provisional application No. 62/055,190, filed on Sep. 25, 2014.

(51) Int. Cl.
*A61F 5/01* (2006.01)
*A61F 13/06* (2006.01)

(52) U.S. Cl.
CPC .......... *A61F 5/0111* (2013.01); *A61F 5/0127* (2013.01); *A61F 13/064* (2013.01); *A61F 13/066* (2013.01)

(58) Field of Classification Search
CPC .... A61F 5/0111; A61F 5/0127; A61F 13/064; A61F 13/066
USPC ...................................... 602/27, 65
See application file for complete search history.

(56) References Cited

U.S. PATENT DOCUMENTS

| 4,597,395 | A | 7/1986 | Barlow et al. |
| 5,000,195 | A | 3/1991 | Neal |
| 5,657,767 | A | 8/1997 | Nelson et al. |
| 5,833,639 | A | 11/1998 | Nunes et al. |
| 6,126,627 | A * | 10/2000 | Brennan ............... A61F 5/0111 602/23 |
| 6,652,474 | B1 | 11/2003 | Quinn et al. |
| 6,663,583 | B1 | 12/2003 | Janis |
| 6,929,617 | B2 | 8/2005 | McCormick et al. |
| 7,094,213 | B1 | 8/2006 | Cook |
| 7,128,725 | B2 | 10/2006 | Rabe |
| 7,497,839 | B2 | 3/2009 | Quinn et al. |
| 8,454,545 | B1 | 6/2013 | Weber et al. |
| 8,512,269 | B1 | 8/2013 | Stano et al. |

(Continued)

OTHER PUBLICATIONS

195R McDavid Level 3 The 195™ Ankle Brace w/ straps, McDavid Company, 2014, www.mcdavidusa.com/Product/195R/MCDAVID_Level_3_The_195%E2%84%A2_Ankle_Brace_w_straps.aspx Retrieved on Jul. 8, 2014.

(Continued)

*Primary Examiner* — Keri J Nelson
(74) *Attorney, Agent, or Firm* — Thorpe North & Western, LLP

(57) ABSTRACT

An ankle support is disclosed and described. The ankle support can include a sleeve that can have a non-stretchable bottom portion to extend under a bottom of a foot. In addition, the sleeve can have side portions extending from the bottom portion to at least an ankle joint. The ankle support can also include non-stretchable support straps connected to the bottom portion, and free ends extending therefrom. In addition, the ankle support can have removable coupling features for the free ends of the support straps located on the side portions. The support straps can cross on a top side of the foot. Along with the bottom portion, the support straps can form a non-stretchable support structure for minimizing movement of the subtalar joint of the ankle.

23 Claims, 6 Drawing Sheets

(56) References Cited

U.S. PATENT DOCUMENTS

| | | |
|---|---|---|
| 8,721,578 B2 * | 5/2014 | Gaylord ................ A61F 5/0102 602/23 |
| 2009/0076428 A1 | 3/2009 | Kay |
| 2014/0114223 A1 | 4/2014 | Ingimundarson |
| 2014/0135675 A1 | 5/2014 | Nayfa |
| 2014/0188026 A1 | 7/2014 | Gaylord |

OTHER PUBLICATIONS

Ankle Brace, Bryanne, 2014, PowerWrap™ Ankle Brace Item #6350 http://bryanne.com/supplies/braces-supports/, Retrieved on Jul. 8, 2014.

* cited by examiner

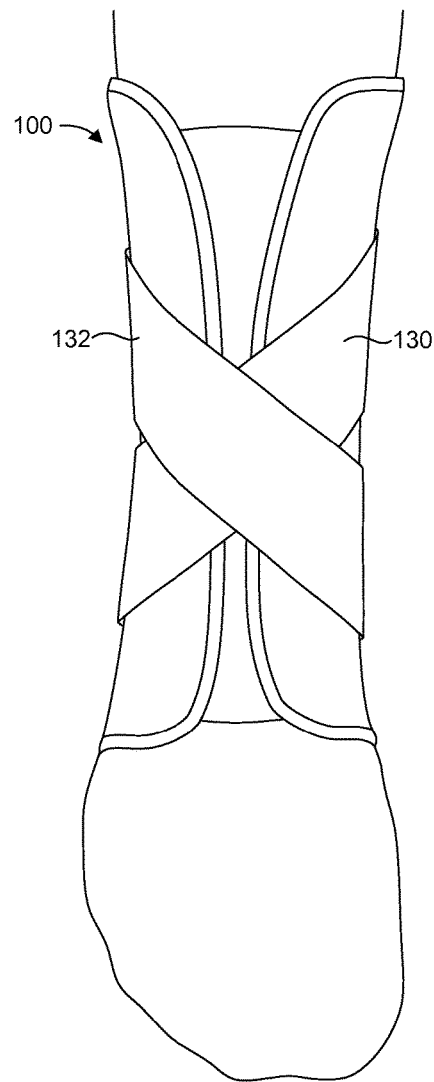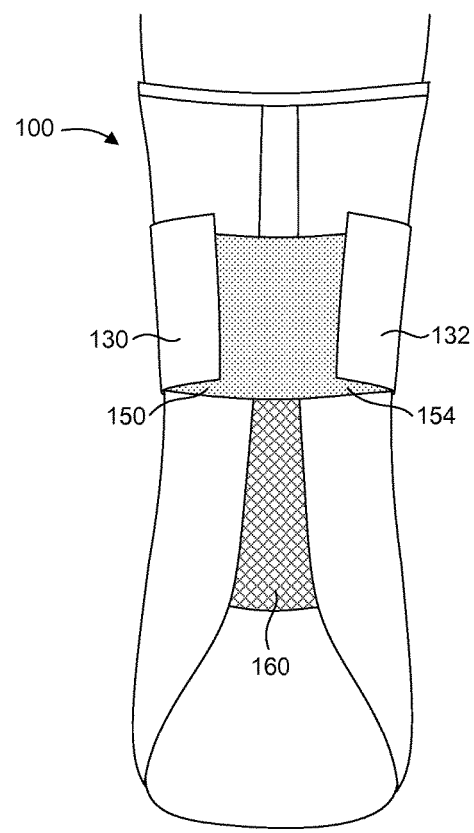
FIG. 6
FIG. 7

ANKLE SUPPORT

RELATED APPLICATION

This application claims the benefit of U.S. Provisional Application No. 62/055,190, filed Sep. 25, 2014, which is incorporated herein by reference.

BACKGROUND

The most common form of ligament injury in ankle sprains is due to an inversion type injury and involves the tearing or complete rupture of the anterior talofibular ligament (ATFL). In more severe ankle sprains, similar damage also occurs to the calcaneofibular ligament (CFL). The ATFL is located on the lateral or outer side of the ankle joint and is connected to the end of the fibula and the talus of the foot. When the ATFL is sprained to a degree that instability of the ankle joint is present, such instability manifests itself by anterior subluxation of the talus. This is often diagnosed by the commonly referred to "drawer test." In this test, the lower area of the shin is held or pushed rearwardly and a horizontal force in a forward direction is applied to heel of the foot. If the ATFL is significantly torn or completely torn, this test reveals a significant degree of anterior displacement of the talus.

Several approaches are currently used in an attempt to prevent or reduce such injuries. A wide variety of ankle braces, wraps and tape are used to allegedly stabilize these joints. Unfortunately, despite such approaches, such ankle injuries remain commonplace and frequently result modest to severe injuries which require extensive rehabilitation and loss of mobility.

SUMMARY

The present disclosure is particularly useful to support the ATFL and/or the CFL in anatomically correct alignments relative to the leg and foot bones of the ankle. Accordingly, an ankle support is disclosed herein. The ankle support can include a sleeve having a non-stretchable bottom portion to extend under a bottom of a foot, and side portions extending from the bottom portion to at least an ankle joint. The ankle support can also include non-stretchable support straps connected to the bottom portion, and having free ends extending therefrom. In addition, the ankle support can include removable coupling features for the free ends of the support straps located on the side portions. The support straps can cross on a top side of the foot and, with the bottom portion, form a non-stretchable support structure for the ankle joint.

In one aspect, an ankle support is disclosed that can include a sleeve adapted to receive and substantially encompass a portion of a foot, an ankle joint, and a portion of a lower leg of a user. The sleeve has a non-stretchable bottom portion which extends under a bottom of the foot, and first and second side portions extending from the bottom portion to above the ankle joint. The ankle support can also include a first non-stretchable support strap having a first connection to the bottom portion, and a first free end extending therefrom. The ankle support can also have a second non-stretchable support strap with a second connection to the bottom portion, and a second free end extending therefrom. In addition, the ankle support can include a first removable coupling feature for the first free end of the first support strap located on the second side portion, and a second removable coupling feature for the second free end of the second support strap located on the first side portion. The first support strap and the second support strap can cross on a top side of the foot and, with the bottom portion, form a non-stretchable support structure for the ankle joint.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 6 is a front view of an ankle support in accordance with an example of the present disclosure.

FIG. 7 is a rear view of an ankle support in accordance with an example of the present disclosure.

Figure 1A:
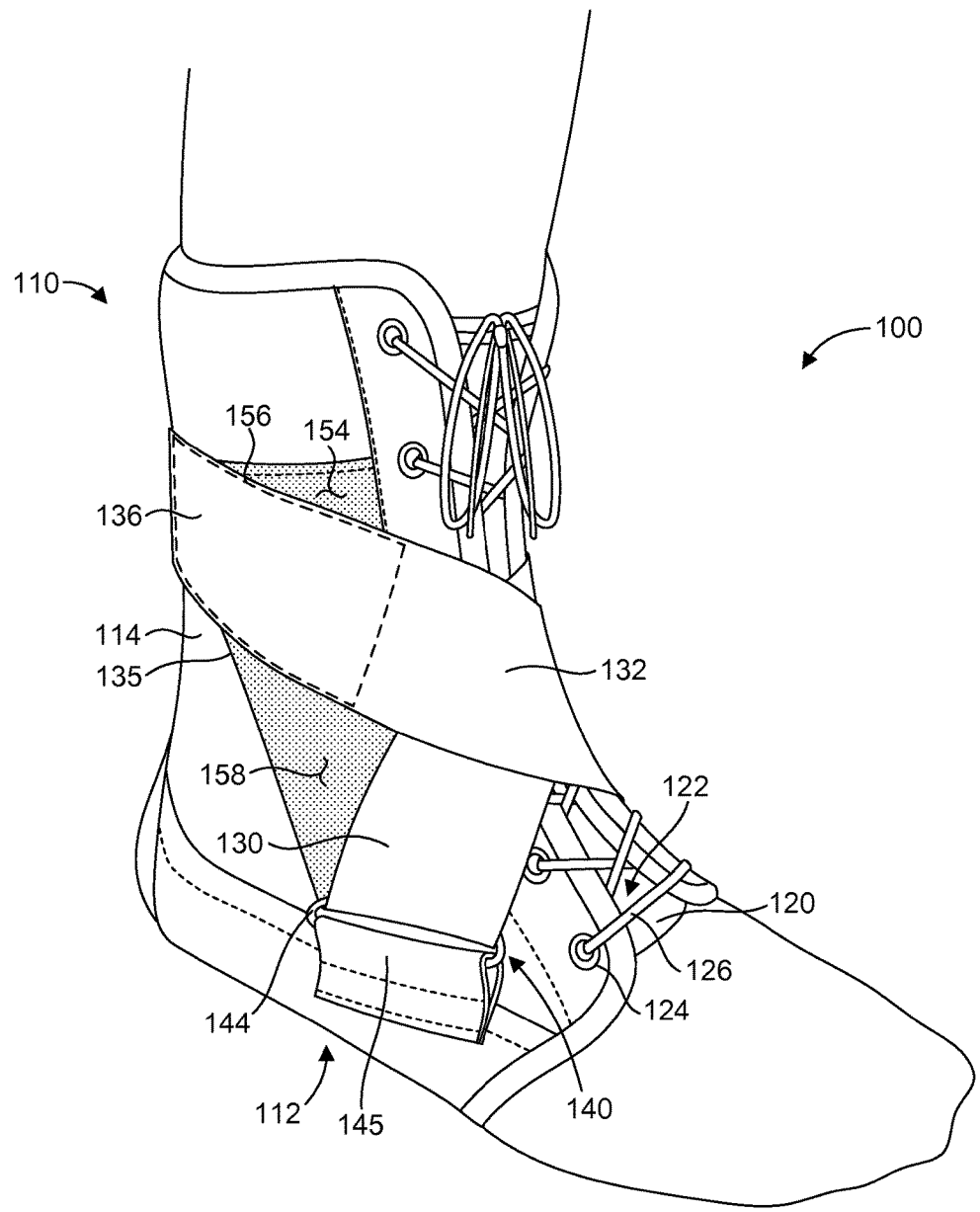
FIG. 1A is a front outside perspective view of an ankle support in accordance with an example of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a seam" includes reference to one or more of such features and reference to "securing" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, or combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Ankle Support

Figure 1B:
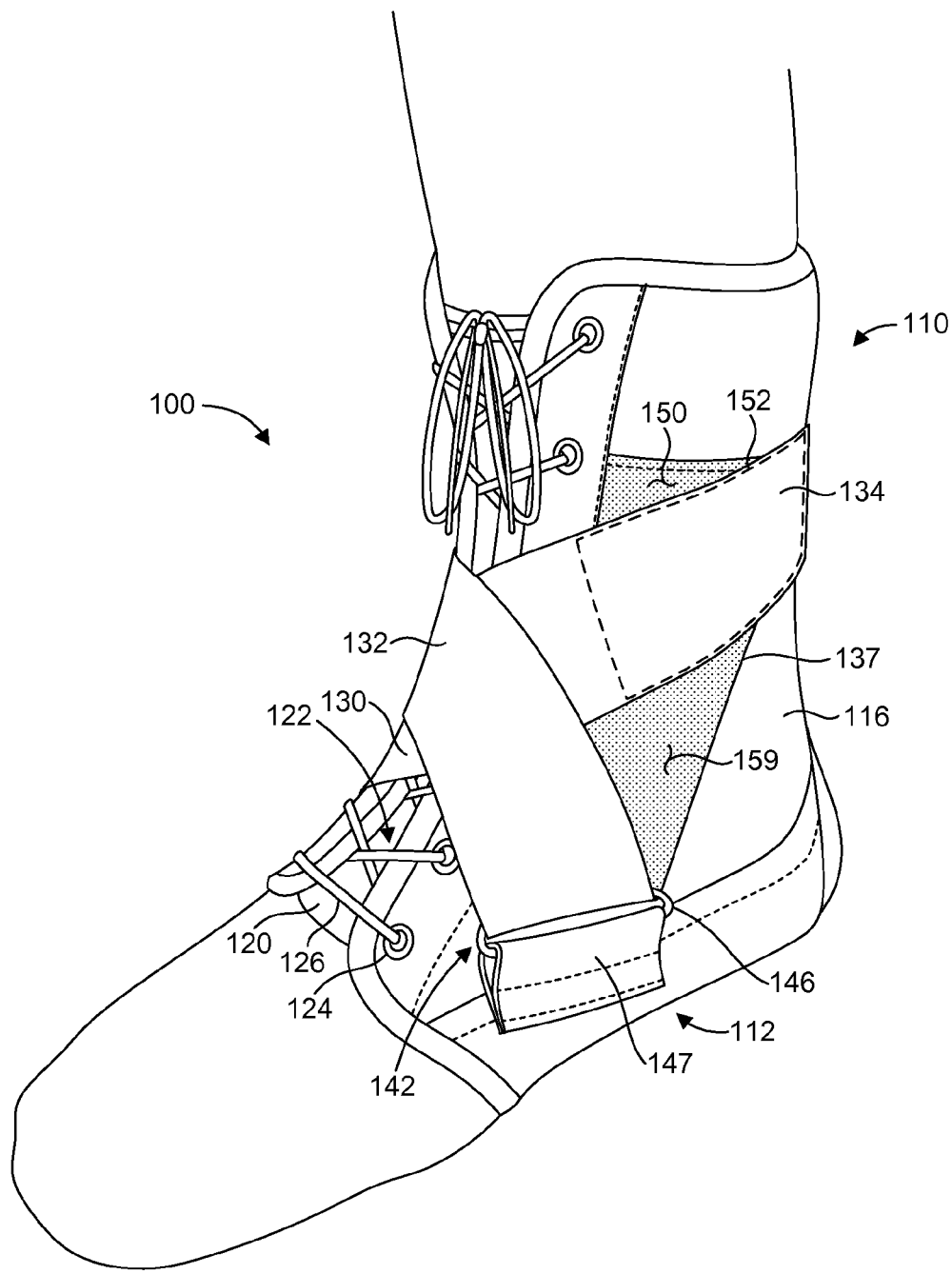
FIG. 1B is a front inside perspective view of the ankle support of FIG. 1A.

FIGS. 1A and 1B illustrate an ankle support 100 in accordance with an example of the present disclosure. The ankle support 100 can be used on previously injured ankles or for proactively protecting ankles against commonly occurring injuries. The ankle support 100 can be readily worn inside a conventional shoe. In one aspect, the features of the ankle support 100 described hereinafter can be constructed or arranged in a symmetric configuration about right and left sides of the ankle support, thus making the ankle support appropriate for use on the right or left foot of a user.

The ankle support 100 can include a sleeve 110 adapted to receive and substantially encompass a portion of a foot, an ankle joint, and a portion of a lower leg of a user, as shown in the figures. The sleeve 110 can have a non-stretchable bottom portion 112 to extend under a bottom of the foot. In one aspect, the bottom portion 112 can be configured to extend at least to opposite sides of the foot, as illustrated.

In addition, the sleeve 110 can have side portions 114 (FIG. 1A), 116 (viewable in FIG. 1B) extending from the bottom portion 112 to at least the ankle joint. As shown in the figures, the side portions 114, 116 extend above the ankle joint, which is obscured from view by the ankle support 100. The side portions 114, 116 of the sleeve 110 can be made of seamed inner and outer layers of nylon or other suitably strong material and with a padding material, such as cotton and/or polyester, arranged between the inner and outer layers. As shown, the sleeve 110 can be shaped as a high-topped shoe that is open about the toe and heel areas. Because the ankle support 100 is open in both the heel and toe areas, the ankle support can be used for a range of foot sizes (e.g. small, large, and extra-large). The front of the sleeve 110 can be open with a tongue 120 that is attached to one or both sides of the sleeve 110 to extend across the front opening 122. In one aspect, the sleeve 110 can have a fastening feature to secure the sleeve about the foot. For example, spaced eyelets 124 can be arranged along opposite sides of the front opening 122 and a fastening feature 126, such as a shoe lace, can be provided for threading through the eyelets to secure the sleeve 110 to the user's foot. The tongue 120 can be formed of stretchable or non-stretchable material.

The ankle support 100 can include non-stretchable support straps 130, 132 connected to the bottom portion 112, and free ends 134 (shown in FIG. 1B), 136 (shown in FIG. 1A) of the support straps can extend from the bottom portion. For example, as shown in FIG. 1A, the ankle support 100 can include the non-stretchable support strap 130 having a connection 140 to the bottom portion 112 on one side of the ankle support. The free end 134 of the support strap 130 can extend from the bottom portion 112 and the connection 140. As shown in FIG. 1B, the ankle support 100 can also include the non-stretchable support strap 132 having a connection 142 to the bottom portion 112 on another side of the ankle support, opposite the side with the connection 142. The free end 136 of the support strap 132 can extend from the bottom portion 112 and the connection 142.

As used herein, the term "non-stretchable" is used to describe a material that can conform to a wearer's foot, ankle, and/or lower leg while having little or no stretch or "give" in normal use of the ankle support 100. Such a non-stretchable material may be strategically utilized in the ankle support 100 as disclosed herein to form a structure that can stabilize the ankle (e.g., the subtalar joint) of the wearer. Suitable non-stretchable materials (e.g., a non-stretch fabric) may be utilized in contrast to a stretchable material (e.g., a stretch fabric) as recognized in the art. Thus, for example, the bottom portion 112 can be made of vinyl, canvas, or any other suitable non-stretchable material. In addition, the support straps 130, 132 can be made of nylon webbing, canvas, or any other suitable non-stretchable material. Generally, the support straps will also include hook and loop fastener (e.g. VELCRO) as described further herein. As a general guideline, a non-stretchable material will have an elongation (i.e. maximum to material failure) of less than 5%, and often less than 3%.

Figure 2:
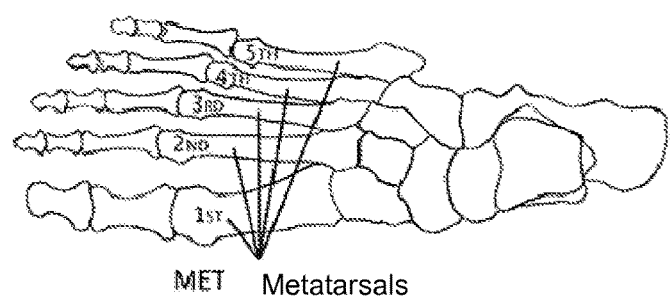
FIG. 2 illustrates metatarsals of a human foot.

In one aspect, the connections 140, 142 of the support straps 130, 132 to the bottom portion 112 can be configured to be proximate first of fifth metatarsal bones of the foot. For example, the connection 140 to the bottom portion 112 can be configured to be proximate a first or fifth metatarsal bone of the foot and in an anterior position relative to the ankle joint. In another aspect, the connection 142 to the bottom portion 112 can be configured to be proximate the other of the first or fifth metatarsal bone of the foot and in an anterior position relative to the ankle joint. The metatarsals of a human foot are illustrated in FIG. 2 for reference.

In one aspect, illustrated in FIGS. 1A and 1B, one or both of the support straps 130, 132 can be slidably connected to the bottom portion 112. In this case, the support strap 130 can have a fixed end 135 coupled to the side portion 114 of the sleeve 110, such as above and/or in an anterior position relative to the ankle joint, and can extend to a sliding connection 140 with the bottom portion 112, with the free end 134 extending from the sliding connection. Similarly, the support strap 132 can have a fixed end 137 coupled to the side portion 116 of the sleeve 110, such as above and/or in an anterior position relative to the ankle joint, and can extend to a sliding connection 142 with the bottom portion 112, with the free end 136 extending from the sliding connection. In such a configuration, the connection 140 and/or the connection 142 can connect the respective strap 130, 132 to the sleeve 110 in a manner that allows for some limited relative movement between the strap and the sleeve. Thus, when the support straps 130, 132 are secured as described hereinafter, the straps can pull forward and downward on the sleeve 110 above and behind the ankle joint to facilitate stabilizing of the subtalar joint of the ankle.

A sliding connection can comprise a ring 144, 146 (e.g., a D-ring or loop of material) coupled to the bottom portion 112 such that the support strap 130, 132 is movable relative to the ring 144, 146, respectively. The ring 144, 146 can provide a connection with the strap 130, 132 by passing the free end 134, 136 of the strap through the ring and turning or bending the strap end back upon itself. The ring 144, 146 can comprise any suitable shape or be constructed of any suitable material. For example, the ring 144, 146 can be constructed of a fabric material and supported such that the ring maintains an elongate configuration, as illustrated, to interface with the width of the strap 130, 132. In one aspect, the ring 144, 146 can be supported and coupled to the bottom portion by a flap 145, 147 of material that is passed through the ring and has its ends anchored at the bottom portion 112 of the sleeve 110. The ring 144, 146 and/or flap 145, 147 can be anchored by thread, by a rivet, or by any other suitable coupling feature. In one aspect, the flap 145, 147 and ring 144, 146 may be arranged to pivot about a rivet to accommodate variations in attachment locations of the free end 134, 136 of the strap 130, 132.

Figure 3:
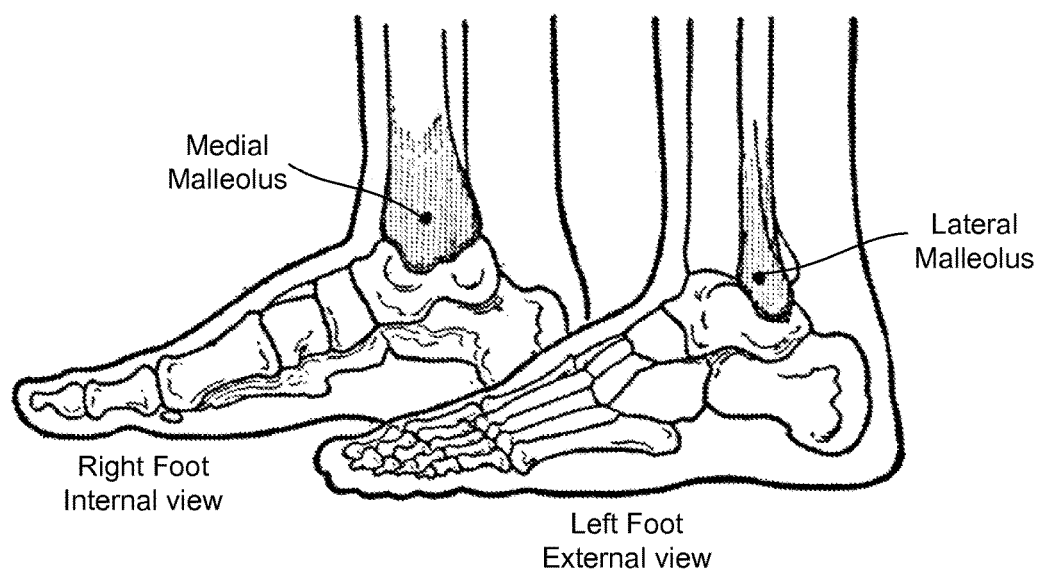
FIG. 3 illustrates medial and lateral malleolus of a human ankle joint.

The fixed end 135, 137 of the support strap 130, 132 can be oriented or positioned on the side portions 114, 116 of the sleeve 110 so as to be adjacent the lateral malleolus or the medial malleolus of the ankle. For example, the fixed end 135 of the support strap 130 can be oriented adjacent a lateral malleolus or a medial malleolus of the ankle joint, and the fixed end 137 of the support strap 132 can be oriented adjacent the other of the lateral malleolus or a medial malleolus of the ankle joint. The medial and lateral malleolus of a human ankle joint are illustrated in FIG. 3 for reference.

Figure 4A:
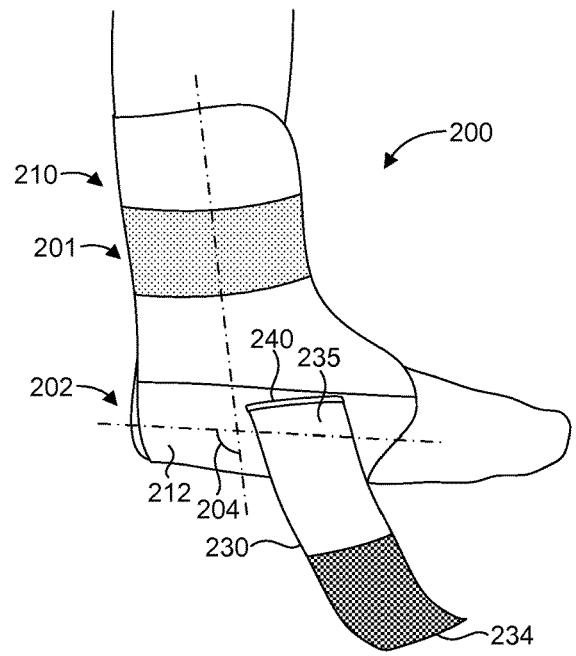
FIGS. 4A and 4B are side perspective views of an ankle support in accordance with another example of the present disclosure.
Figure 4B:
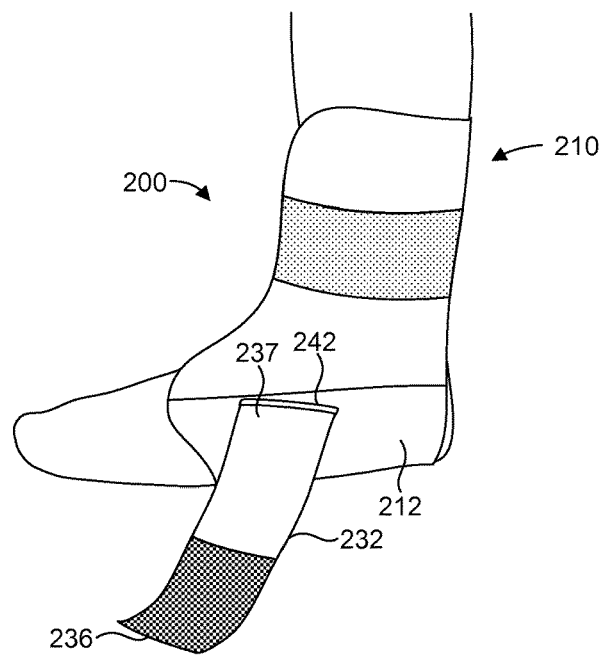

In one aspect, shown the ankle support 200 of FIGS. 4A and 4B, a connection of a support strap to the bottom portion of a sleeve can be a fixed connection. For example, a support strap 230 can be fixedly connected 240 to a bottom portion 212 of a sleeve 210, such that the strap originates from the bottom portion. Thus, a fixed end 235 of the strap 230 can be secured to the bottom portion 212 at the fixed connection 240 and a free end 234 of the strap can extend from the fixed connection. Similarly, a support strap 232 can be fixedly connected 242 to the bottom portion 212 of the sleeve 210, such that the strap originates from the bottom portion. Thus, a fixed end 237 of the strap 232 can be secured to the bottom portion 212 at the fixed connection 242 and a free end 236 of the strap can extend from the fixed connection.

In one aspect, an ankle brace, such as the ankle brace 200 shown in FIG. 4A, can have any suitable angle 204 between an upper portion 201 and a lower portion 202 of the ankle brace. In one aspect, the angle 204 can be less than 90 degrees. In another aspect, the angle 204 can be greater than 90 degrees. In yet another aspect, the angle 204 can be equal to 90 degrees. With the angle 204 equal to or within about 10 degrees and most often within about 5 degrees of 90 degrees, bunching of material during use may be minimized when the straps are secured about the user's foot.

With further reference to FIGS. 1A and 1B, the ankle support 100 can also include removable coupling features for the free ends 134, 136 of the support straps 130, 132, which can be located on the side portions 114, 116 of the sleeve 110. For example, to secure the support strap 130, the ankle support 100 can have a removable coupling feature 150 for the free end 134 of the support strap 130 located on the side portion 116, as shown in FIG. 1B. The free end 134 of the support strap 130 can include a complementary or mating removable coupling feature 152 (hidden from view but identified by broken lines) to removably couple with the removable coupling feature 150. Similarly, to secure the support strap 132, the ankle support 100 can also have a removable coupling feature 154 for the free end 136 of the support strap 132 located on the side portion 114, as shown in FIG. 1A. The free end 136 of the support strap 132 can include a complementary or mating removable coupling feature 156 (hidden from view but identified by broken lines) to removably couple with the removable coupling feature 154. Additional coupling features 158, 159 can be located on the straps 130, 132 to provide additional coupling options and/or surface area for securing the free ends 136, 134 of the straps 132, 130. The removable coupling features 150, 152, 154, 156, 158, 159 can comprise any suitable coupling feature, such as a hook and loop fastener, to secure the free end 134, 136 of the strap 130, 132 to the side portion 114, 116, respectively, after the strap 130, 132 has been pulled tight. In one aspect, the removable coupling feature 150 and/or the removable coupling feature 154 can be located on the side portion 114, 116 above and/or in an anterior position relative to the ankle joint. Thus, when the support straps 130, 132 are secured in place, an X-shape is formed across a front of the ankle support 100 adjacent a bottom end of the tibia just above the ankle joint. In this manner, the support straps 130, 132 can be anchored to positions adjacent the lateral malleolus and the medial malleolus, respectively, in order to minimize movement of the subtalar joint.

Figure 5A:
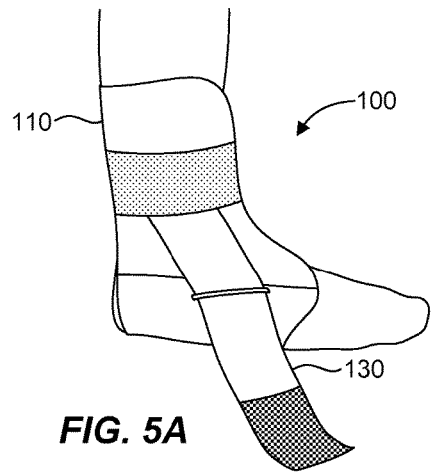
FIG. 5A is a side view of an ankle support showing an unsecured free end of a first support strap, in accordance with an example of the present disclosure.
Figure 5B:
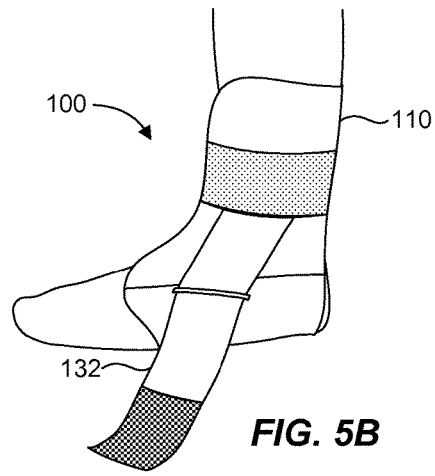
FIG. 5B is a side view of the ankle support of FIG. 5A, illustrating an opposite side and showing an unsecured free end of a second support strap, in accordance with an example of the present disclosure.
Figure 5C:
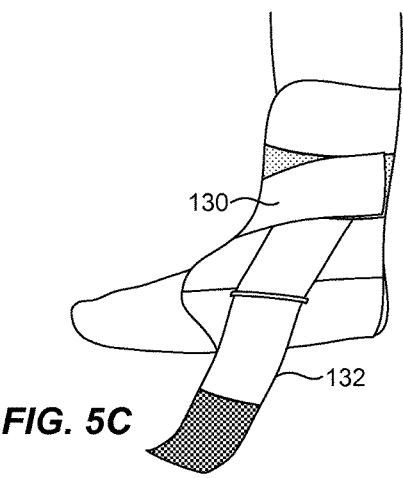
FIG. 5C is a side view of the ankle support of FIG. 5A, showing the free end of the first support strap secured with a removable coupling feature, in accordance with an example of the present disclosure.
Figure 5D:
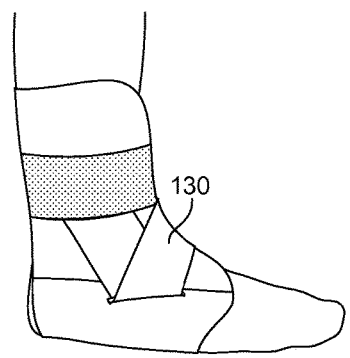
FIG. 5D is an opposite side view of the ankle support configuration of FIG. 5C, showing a removable coupling feature for securing the free end of the second support strap, in accordance with an example of the present disclosure.
Figure 5E:
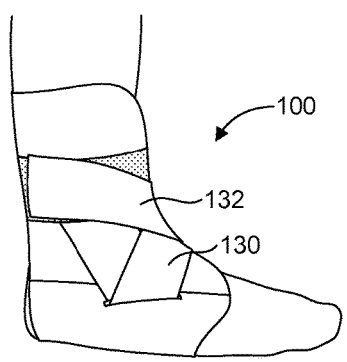
FIG. 5E is a side view of the ankle support of FIG. 5A, showing the free end of the second support strap secured with the removable coupling feature, in accordance with an example of the present disclosure.

In use, the ankle support 100 can be placed on either foot of a user in a conventional fashion by inserting the toes and forefoot through the frontal opening for the toes with the heel extending through the opening for the heel at a lower rear of the sleeve 110. The tongue 120 can be positioned over the instep and front ankle area in a conventional manner and then the lace 126 may be drawn tight and tied. Appropriately positioning and tightening the lace 126 can assure that the sleeve 110 is snugly fitted over the foot and ankle joint, to arrive at the configurations shown in FIGS. 5A and 5B. FIGS. 5A-5E are simplified representations of the ankle support 100 shown in FIGS. 1A and 1B and therefore utilize reference numbers consistent with FIGS. 1A and 1B. Next, in either order, each support strap 130, 132 can be pulled tight and secured across the front, top side of the foot. For example, the support strap 130 can be secured as shown in FIGS. 5C and 5D and the support strap 132 can be secured in a similar manner such that the straps 130, 132 overlap and the ankle support 100 is secured about the foot as shown in FIG. 5E. When the support straps 130, 132 are secured in place, an X-shape is formed across a front of the ankle support 100 as shown in FIG. 6.

Generally, the ankle support 100 can have a low profile across portions of the support, including support straps 130, 132, sleeve 110 (e.g., sides 114, 116 and bottom 112), and connections 140, 142. Specifically, the ankle support 100 can include portions which exhibit widths from about 2 mm to about 10 mm. Most often the ankle support 100 including support straps 130, 132, sleeve 110 (e.g., sides 114, 116 and bottom 112), and connections 140, 142, when the straps 130, 132 are engaged, can have an overall thickness from about 3 mm to about 6 mm. Each connection 140, 142 can often add no more than about 4 mm, and in some cases less than 3 mm to the overall thickness.

As shown in FIG. 7, a rear of the ankle support 100 can include an elastic material 160 to improve fit and comfort for the wearer. The elastic material 160 can be disposed in any suitable location. As shown in the figure, the elastic material 160 is located between the side portions 114, 116 above an opening for the heel and extending as a slit to a top portion of the sleeve, which can provide comfort for an Achilles tendon of the wearer. In one aspect, the removable coupling features 150, 154 can extend around the rear of the ankle support 100 to provide additional area for coupling with the support straps 130, 132.

An ankle support of the present disclosure provides several advantages for supporting the subtalar joint. In general, an ankle support in accordance with the present disclosure can restrict the degree of displacement of the ankle bones of the wearer in both vertical and horizontal directions, and particularly with respect to inversion moment. This provides positive support particularly to the ATFL and CFL by resisting forces applied to the ankle joint that tend to place undue strain on these ligaments. For example, the bottom portion 112 and the support straps 130, 132, which cross on a top side of the foot, can form a non-stretchable support structure (i.e., due to the non-stretchable materials) for the subtalar joint that can support a load tending to cause eversion or inversion instead of subjecting the ATFL and/or CFL to the load. In addition, as illustrated in the figures (e.g., FIG. 6), the support strap 130 and the support strap 132 can cross on a front, top side of the foot, which can also support a load tending to cause eversion or inversion of the foot. Thus, in one aspect, neither of the support straps 130, 132 extends behind or around a back of the ankle joint, as is evident in FIG. 7. Furthermore, unlike merely wrapping a foot, which allows for some sliding or relative movement between the wrap and the foot, the support straps 130, 132 disclosed herein can be secured to a location on the bottom portion 112 of the sleeve 110 to maintain a relative position of the straps 130, 132 about the foot and to reduce or prevent inversion moment of the subtalar joint. Thus, in another aspect, neither of the support straps 130, 132 extends under the foot or, in other words, under the bottom portion 112 of the ankle support 100. The configuration and attachment points of the stabilizing support straps 130, 132 and the bottom portion 112 of the ankle support 100 can thus provide an improved degree of positive support to the ATFL and restrict anterior displacement of the talus bone under the fibula, which occurs when the ATFL becomes torn or completely ruptured.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. An ankle support, comprising:
a sleeve adapted to receive and substantially encompass a portion of a foot, an ankle joint, and a portion of a lower leg of a user, the sleeve having a non-stretchable bottom portion to extend under a bottom of the foot, and first and second side portions configured to extend from the bottom portion to above the ankle joint;
a first non-stretchable support strap having a first connection to the bottom portion, and a first free end extending therefrom;
a second non-stretchable support strap having a second connection to the bottom portion, and a second free end extending therefrom, wherein at least one of the first connection and the second connection comprises a sliding connection;
a first removable coupling feature for the first free end of the first support strap located on the second side portion; and
a second removable coupling feature for the second free end of the second support strap located on the first side portion,
wherein the first support strap and the second support strap are configured to cross on a top side of the foot and, with the bottom portion, form a non-stretchable support structure for the ankle joint, and
wherein the first support strap comprises a first fixed end coupled to the first side portion of the sleeve and extends from the first connection to the first free end, and wherein the first fixed end of the first support strap is configured to be oriented adjacent a lateral malleolus or a medial malleolus of the ankle joint and wherein the first fixed end of the first support strap is coupled to the first side portion of the sleeve configured to be above the ankle joint.

2. The ankle support of claim 1, wherein at least one of the first connection and the second connection comprises a fixed connection.

3. The ankle support of claim 1, wherein the sliding connection comprises a ring coupled to the bottom portion such that the first or second support strap is movable relative to the ring.

4. The ankle support of claim 1, wherein the second support strap comprises a second fixed end coupled to the second side portion of the sleeve and extends from the second connection to the second free end.

5. The ankle support of claim 4, wherein the second fixed end of the second support strap is coupled to the second side portion of the sleeve configured to be above the ankle joint.

6. The ankle support of claim 4, wherein the second fixed end of the second support strap is configured to be oriented adjacent a lateral malleolus or a medial malleolus of the ankle joint.

7. The ankle support of claim 1, wherein the first connection and the second connection to the bottom portion are each configured to be proximate a first or a fifth metatarsal bone of the foot.

8. The ankle support of claim 1, wherein the first removable coupling feature is located on the second side portion configured to be above the ankle joint and the second removable coupling feature is located on the first side portion configured to be above the ankle joint.

9. The ankle support of claim 1, wherein at least one of the first and second removable coupling features comprises a hook and loop fastener.

10. The ankle support of claim 1, wherein the bottom portion is configured to extend at least to opposite sides of the foot.

11. The ankle support of claim 1, wherein neither of the first support strap and the second support strap are configured to extend around a back of the ankle joint.

12. The ankle support of claim 1, wherein neither of the first support strap and the second support strap are configured to extend under the bottom of the foot.

13. An ankle support, comprising:
a sleeve adapted to receive and substantially encompass a portion of a foot, an ankle joint, and a portion of a lower leg of a user, the sleeve having a non-stretchable bottom portion to extend under a bottom of the foot, and first and second side portions configured to extend from the bottom portion to above the ankle joint;
a first non-stretchable support strap having a first connection to the bottom portion, and a first free end extending therefrom;
a second non-stretchable support strap having a second connection to the bottom portion, and a second free end extending therefrom, wherein at least one of the first connection and the second connection comprises a sliding connection;
a first removable coupling feature for the first free end of the first support strap located on the second side portion; and
a second removable coupling feature for the second free end of the second support strap located on the first side portion,
wherein the first support strap and the second support strap are configured to cross on a top side of the foot and, with the bottom portion, form a non-stretchable support structure for the ankle joint,
wherein the first support strap comprises a first fixed end coupled to the first side portion of the sleeve and extends from the first connection to the first free end, and wherein the first fixed end of the first support strap is configured to be oriented adjacent a lateral malleolus or a medial malleolus of the ankle joint,
wherein the second support strap comprises a second fixed end coupled to the second side portion of the sleeve and extends from the second connection to the second free end, and
wherein the second fixed end of the second support strap is coupled to the second side portion of the sleeve configured to be above the ankle joint.

14. The ankle support of claim 13, wherein at least one of the first connection and the second connection comprises a fixed connection.

15. The ankle support of claim 13, wherein the sliding connection comprises a ring coupled to the bottom portion such that the first or second support strap is movable relative to the ring.

16. The ankle support of claim 13, wherein the first fixed end of the first support strap is coupled to the first side portion of the sleeve configured to be above the ankle joint.

17. The ankle support of claim 13, wherein the second fixed end of the second support strap is configured to be oriented adjacent a lateral malleolus or a medial malleolus of the ankle joint.

18. The ankle support of claim 13, wherein the first connection and the second connection to the bottom portion are each configured to be proximate a first or a fifth metatarsal bone of the foot.

19. The ankle support of claim 13, wherein the first removable coupling feature is located on the second side portion configured to be above the ankle joint and the second removable coupling feature is located on the first side portion configured to be above the ankle joint.

20. The ankle support of claim 13, wherein at least one of the first and second removable coupling features comprises a hook and loop fastener.

21. The ankle support of claim 13, wherein the bottom portion is configured to extend at least to opposite sides of the foot.

22. The ankle support of claim 13, wherein neither of the first support strap and the second support strap are configured to extend around a back of the ankle joint.

23. The ankle support of claim 13, wherein neither of the first support strap and the second support strap are configured to extend under the bottom of the foot.

* * * * *